(12) United States Patent
Pitcher et al.

(10) Patent No.: US 10,806,768 B2
(45) Date of Patent: Oct. 20, 2020

(54) COMPOSITION FOR PROMOTING METALLOTHIONEIN PRODUCTION

(71) Applicants: Stephen N. Pitcher, Alpine, UT (US); Danny Purser, Provo, UT (US)

(72) Inventors: Stephen N. Pitcher, Alpine, UT (US); Danny Purser, Provo, UT (US)

(*) Notice: Subject to any disclaimer, the term of this patent is extended or adjusted under 35 U.S.C. 154(b) by 12 days.

(21) Appl. No.: 15/607,420

(22) Filed: May 26, 2017

(65) Prior Publication Data

US 2017/0340694 A1 Nov. 30, 2017

Related U.S. Application Data

(60) Provisional application No. 62/342,113, filed on May 26, 2016.

(51) Int. Cl.

| | | |
|---|---|---|
| A61K 38/06 | (2006.01) | |
| A61K 31/198 | (2006.01) | |
| A61K 33/24 | (2019.01) | |
| A61K 31/4415 | (2006.01) | |
| A61K 33/30 | (2006.01) | |
| A61K 33/22 | (2006.01) | |
| A61K 31/717 | (2006.01) | |
| A61K 33/42 | (2006.01) | |
| A61K 33/06 | (2006.01) | |

(52) U.S. Cl.
CPC .......... *A61K 38/063* (2013.01); *A61K 31/198* (2013.01); *A61K 31/4415* (2013.01); *A61K 31/717* (2013.01); *A61K 33/06* (2013.01); *A61K 33/22* (2013.01); *A61K 33/24* (2013.01); *A61K 33/30* (2013.01); *A61K 33/42* (2013.01)

(58) Field of Classification Search
CPC ...... A61K 38/063; A61K 33/42; A61K 31/20; A61K 31/717; A61K 33/22; A61K 31/4415; A61K 33/24; A61K 31/198; A61K 33/30; A61K 33/06
See application file for complete search history.

(56) References Cited

U.S. PATENT DOCUMENTS

| | | | | |
|---|---|---|---|---|
| 2002/0176900 A1* | 11/2002 | Yegorova | ............. | A61K 31/555 424/754 |
| 2002/0182196 A1* | 12/2002 | McCleary | ............. | A61K 31/00 424/94.1 |
| 2004/0197430 A1* | 10/2004 | Meyrowitz | .......... | A61K 36/258 424/756 |
| 2006/0099239 A1* | 5/2006 | Coleman | ................ | A23G 3/368 424/440 |
| 2006/0134300 A1* | 6/2006 | Newman | ................. | A23F 5/243 426/590 |
| 2008/0038367 A1* | 2/2008 | Saloum | ............... | A61K 36/185 424/617 |
| 2009/0011047 A1* | 1/2009 | Rademaker | ............ | A61K 33/36 424/624 |
| 2010/0190739 A1* | 7/2010 | Sutterer | ................. | A61K 31/07 514/52 |
| 2011/0237525 A1* | 9/2011 | Haley | ................. | A61K 9/0014 514/21.9 |
| 2015/0216213 A1* | 8/2015 | Sizer | ...................... | A23L 33/40 426/73 |

* cited by examiner

*Primary Examiner* — Snigdha Maewall
(74) *Attorney, Agent, or Firm* — Terrence J. Edwards; TechLaw Ventures, PLLC

(57) ABSTRACT

The present disclosure relates to a composition to aid in heavy metal detox. Metallothioneins (MT) are a family of cysteine-rich enzymes in the body that help remove and regulate heavy metals, copper, and other metals. Amino Acids in combination with zinc and/or molybdenum may provide improved production of MT over amino acid or zinc supplements alone. Additionally, Vitamin B6, Molybdenum, and Boron may be included to further enhance the efficacy of the composition.

18 Claims, No Drawings

COMPOSITION FOR PROMOTING METALLOTHIONEIN PRODUCTION

PRIORITY

This application claims priority to U.S. Provisional Patent Application No. 62/342,113, filed on 26 May 2016, which is hereby incorporated by reference in its entirety.

BACKGROUND

The present disclosure relates to a bioeffective composition. Specifically, this disclosure relates to a composition comprising zinc, molybdenum, and amino acids. As such, the composition may be effective to increase production and activity of metallothioneins (MT) and reduce heavy metal accumulations in tissue.

Excess heavy metals in the body have been shown to cause a number of physical problems, and in the case of certain heavy metals such as arsenic, death. Heavy metal and copper toxicity have been associated with causing a number of physical problems such as muscle wasting, hypogonadism, trigger point formation, fibromyalgia symptoms, and various forms of neuropathy.

Science is continually expanding an understanding of the mechanisms organisms use to regulate and rid themselves of excess or unwanted compounds and elements. Proper levels of many necessary elements and compounds are critical to health. About 25 elements are known to be necessary (physiological) to sustain human life, each playing a major or minor role in one or more essential biological processes. Too little or too much of these essential elements may lead to debilitating consequences or death if the imbalance persists. Other unnecessary elements (xenobiotic) may be present if ingested or inhaled that may be harmful if not purged by the body, such as Mercury, Lead, Aluminum, Cadmium, and even Arsenic, which may be present in trace amounts is many foods humans eat.

The ability to effectively and efficiently manage the levels of the essential and non-essential elements leads to good health by avoiding the many problems that might otherwise arise from imbalances. Efforts to understand and positively affect element balance and management should be an ongoing and encouraged activity in biological, medical, supplemental, and food sciences to promote overall health.

BRIEF SUMMARY

The present disclosure relates to a composition to aid in heavy metal detox and promotion of health biological homeostasis. Metallothioneins (MT) are a family of cysteine-rich enzymes in the body that help remove and regulate heavy metals, copper, and other metals, and help to promote healthy cellular homeostasis. Amino acids in combination with zinc and/or molybdenum may provide improved results of production and activity of MT over amino acid or zinc and/or molybdenum supplements alone. Additionally, Vitamin B6, boron, and other minerals, elements and compounds may be included to further enhance the efficacy of the composition.

DETAILED DESCRIPTION

The present disclosure relates to a composition to aid in heavy metal detox and biological healthy homeostasis. Metallothioneins (MT) are a family of cysteine-rich enzymes in the body that help remove and regulate heavy metals, copper, and other metals. MT have the capacity to bind both necessary physiological metals (i.e. zinc, copper, selenium) and xenobiotic elements (i.e. cadmium, mercury, silver, arsenic) through the thiol group of its cysteine residues, which may represent nearly 30% of constituent amino acid residues. MT form main isoforms expressed in humans: MT1, MT2, MT3, and MT4. MT functions are not completely known or understood, but MT may provide protection against metal toxicity through the binding function, and have been shown to be integral in regulation of proper levels of physiological metals. Importantly, MT may also provide some protection against oxidative stress.

Presence and availability of amino acids are known to promote the production of MT. Some amino acids include N-Acetyl LCysteine (NAC), Serine, and Glutamine. These amino acids also help form glutathione which is critical to the conjugation and removal of heavy metals. Over time, and due to inadequate zinc, molybdenum, or Vitamin B6 intake, or a lack of key amino acids (such as cysteine or NAC) in the diet, MT levels can decline, or the MT can malfunction or under-function causing a build-up or improper balance or accumulation of metals (non-ceruoplasmin-bound copper or NCC is commonly used as a proxy).

Excessive non-ceruloplasmin bound copper (NCC) has even been shown to be a possible cause of trigger points, the main diagnostic sign, symptom, and criteria in myofascial pain syndrome (i.e. fibromyalgia). In mammalian pathways, copper is partially detoxified through sequestration of in the metal-binding and transporting metallothioneins. Ceruloplasmin, a carrier of copper, is critical in the handling of copper in the human body and requires boron.

Higher levels of MT have been shown to be effective in aiding the body to maintain a proper balance of copper and other physiological essential metals, while assisting in binding and ridding the body of other dangerous xenobiotic heavy metals such as arsenic. In the human body, large quantities of MT are synthesized primarily in the liver and kidneys. Their production is known to be dependent of availability of certain dietary minerals such as zinc, copper, and selenium, or the presence of amino acids histidine and cysteine, and on stresses, such as cold and heat stress.

Zinc supplements have been used for many years to help with a variety of health issues. Zinc is known to be necessary for many different physiological functions, including important protein synthesis, immune system maintenance, diabetes control, wound management, etc. Because MT production may be affected by the presence of zinc, zinc and amino acids were combined in a dietary supplement together. Through experimentation, combinations of zinc, Vitamin B6, Molybdenum, and amino acids were identified that unexpectedly exhibited much greater results in combination in promoting production of MT than any of zinc, Vitamin B6, Molybdenum, or amino acids alone.

EXAMPLES

Throughout this specification, compositions may be discussed that contain ranges of various ingredients in the overall compositions. These ranges may be defined by upper and lower boundaries. Each lower boundary can be combined with each upper boundary to define a range. The lower and upper boundaries should each be taken as a separate element.

In general, the disclosed embodiments may provide certain formulae and combinations of ingredients that provide for increased effectiveness in the known benefits of zinc, Vitamin B6, molybdenum, or amino acids alone. Some aspects of the disclosed embodiments may provide various nutraceutical compositions, which may include various elements and ingredients, such as combinations of amino acids, which have been found to be effective. Thus, while the disclosed embodiments may disclose specific examples of known nutraceutical compositions and combined nutraceutical elements, one having skill in the art will appreciate that the specific components of the disclosed embodiments may be substituted with natural or synthetic equivalents to achieve a desired results within the spirit and teaching of the disclosed embodiments. Furthermore, other non-essential ingredients, such as binders, bulking agents, flavors, or other known nutraceutical compounds may be added. Other elements and agents may be added to assist one or more essential ingredients, such as boron to assist the biofuncionality of ceruoplasmin in carrying copper. Accordingly, the specific embodiments provided are not intended to be limiting, but rather are provided examples disclosing and teaching the underlying principles. Each of the compounds and elements used in the specific examples below were initially selected due to known benefits, interactions with other included components, or in an effort to determine efficacy through experimentation.

Metallothioneins and the metal binding systems critically require certain key substances to function—such as vitamin B6, zinc, molybdenum, and certain key amino acids, and a deficiency of any of these substances causes the process to be dysfunctional. The known Recommended Daily Amount for Adults are: Zinc RDA (Adults) Approximately 10 mg per day; Boron RDA (Adults) 20 mg per day (est); and Vitamin B6 (pyridoxine) 1.3 mg per day.

Zinc

Zinc is inherently involved in the function of metallothioneins and in the utilization of Vitamin B6 (pyridoxine), as a matter of fact the two appear to go hand in hand through the utilization of copper in human physiology. In one study involving B6 deficient rats, the zinc status was assessed by measuring their erythrocyte zinc-metallothionein-1 (Zn-MT-1) and plasma zinc levels. A significant difference ($p<0.001$) in plasma zinc levels was observed between the B6 deficient group and the control and pair-fed groups (1.35 micrograms/ml+/−0.08, 1.99 micrograms/ml+/−0.06 and 2.03 micrograms/ml+/−0.07 respectively). Erythrocyte Zn-MT-1 levels were significantly lower in vitamin B6 deficient rats when compared to control animals. So B6 deficiency in the diet may affect the very important zinc-based metallothioneins, and also reduce the level of zinc in the body.

As your body gets depleted of zinc (for whatever reason), by necessity it chooses to replace the missing zinc with the next nearest (next door in periodic table of elements) almost similar metal, which is copper. Excess very inflammatory copper, however, is not an optimal choice due to the problems it causes.

Vitamin B6

Pyridoxine (Vitamin B6) is an important piece of the metallothionein support supplement panorama. First, zinc is inherently involved in the B6 utilization process. Pyridoxal kinase, a key enzyme in the formation of vitamin B6 coenzymes, requires a zinc-ATP complex as a substrate. Recent findings show that zinc-metallothionein facilitates the formation of the zinc-ATP complex. Thus, the concentration of zinc-metallothionein in tissues may serve in the regulation of vitamin B6 metabolism.

A deficiency of B6 causes an imbalance of zinc and copper—mostly a decrease in zinc levels and copper levels, coupled with an increased excretion of zinc and copper. This indicates gross worsening of metallothionein dysfunction in these types of individuals. So, zinc needs B6 and B6 needs zinc, while metallothioneins need both.

Molybdenum

Physiologic metals such as copper, zinc, and molybdenum are inherently involved in their individual functions. Molybdenum is critical to the function of all metallothioneins, but especially with cuprothionein as it forms a cofactor, molybdopterin, which is helpful in the mobilization of metals such as copper in the human body. The molybdenum cofactor, in its totality, consists of molybdopterin, a phosphorylated pyranopterin, with an ene-dithiolate coordinating molybdenum[12] which allows that formation of cuprothionein.

More research has shown how important molybdenum is to copper. The transition element molybdenum (Mo) is of essential importance for nearly all biological systems as it is required by enzymes catalyzing diverse key reactions in the global carbon, sulfur and nitrogen metabolism. The metal itself is biologically inactive unless it is complexed by a special cofactor. With the exception of bacterial nitrogenase, where Mo is a constituent of the FeMo-cofactor, Mo is bound to a pterin, thus forming the molybdenum cofactor (Moco) which is the active compound at the catalytic site of all other Mo-enzymes. In eukaryotes, the most prominent Mo-enzymes are: (1) sulfite oxidase, which catalyzes the final step in the degradation of sulfur-containing amino acids and is involved in detoxifying excess sulfite; (2) xanthine dehydrogenase, which is involved in purine catabolism and reactive oxygen production; (3) aldehyde oxidase, which oxidizes a variety of aldehydes and is essential for the biosynthesis of the phytohormone abscisic acid, and in autotrophic organisms also; and (4) nitrate reductase, which catalyzes the key step in inorganic nitrogen assimilation.

All Mo-enzymes, except plant sulfite oxidase, need at least one more redox active center, many of them involving iron in electron transfer. The biosynthesis of Moco involves the complex interaction of six proteins and is a process of four steps, which also includes iron as well as copper in an indispensable way. Moco as released after synthesis is likely to be distributed to the apoproteins of Mo-enzymes by putative Moco-carrier proteins. Xanthine dehydrogenase and aldehyde oxidase, but not sulfite oxidase and nitrate reductase, require the post-translational sulfuration of their Mo-site for becoming active. This final maturation step is catalyzed by a Moco-sulfurase enzyme, which mobilizes sulfur from 1-cysteine in a pyridoxal phosphate-dependent manner as typical for cysteine desulfurases.

Boron

The Boron RDA is usually considered to be 3 mg/day. Though not considered an essential vitamin or mineral, there is some evidence to suggest that it may be. From studies, we know that boron is critical to ceruloplasmin functionality and levels—boron depletion leads to lower ceruloplasmin level, which can dramatically change the NCC results. Boron seems to aid in the formation of steroid hormones (estrogen) and vitamin D and estrogen, and it improves copper metabolism, while a decrease in boron tends to cause an increase in free copper levels.

Serine

Serine, though a non-essential amino acid, is critical in the homocysteine pathway for glutathione formation, which in turn is important in the formation of functional metallothioneins. Serine is also helpful in the treatment of fibromyalgia and has been shown to be low in sufferers of the disease.

Glutamine

Glutamine, like serine, is critical in the homocysteine pathway for glutathione formation. The functions of glutamine/glutamate are many, i.e., they are substrates for protein synthesis, anabolic precursors for muscle growth, they regulate acid-base balance in the kidney, they are substrates for ureagenesis in the liver and for hepatic and renal gluconeogenesis, they act as an oxidative fuel for the intestine and cells of the immune system, provide inter-organ nitrogen transport, and act as precursors of neurotransmitter synthesis, of nucleotide and nucleic acid synthesis and of glutathione production.

Cysteine (NAC)

N-Acetyl-Cysteine (NAC) is the rate limiting amino acid for the formation of glutathione. If someone is low in NAC then the production of glutathione is limited. But this only true in people who are not genetically impaired with a reduction in key glutathione redox enzymes. In one peer reviewed study there was no statistically significant difference between the NAC and placebo groups on the CGI-I ($p>0.69$) but the glutathione (GSH) level in blood was significantly higher in the NAC group ($p<0.05$). The oxidative glutathione disulfide (GSSG) level increased in the NAC group, however only at a trend level of significance ($p=0.09$). There was no significant difference between the NAC and placebo groups in the GSH/GSSG ratio, DNA strand break and oxidative damage, and blood homocysteine levels at week 12. This result means no significant change in GSH levels in these patients. As such, these patients and many other people have a problem not with forming glutathione, but reducing it.

Glutathione (GSH)

Glutathione is an antioxidant formed from three amino acids—cysteine, glycine, and glutamine. GSH is critical to the function of metallothioneins and makes up approximately a third of the molecular weight of the molecule—this hand-in-hand working together of GSH and metallothioneins is especially critical in preventing copper toxicity. The main problem with most people is not the lack of cysteine in their diet, but genetic issues with reducing glutathione back to the functional reduced form of GSH.

Example 1

Some embodiments a heavy metal detoxification compositions may include
1) bio-available form of zinc,
2) Vitamin B6,
3) bio-available form of molybdenum,
4) amino acids
5) Cellulose
6) Magnesium Stearate
7) Dicalcium Phospahate In some embodiments, one dose may include the following amounts or ranges of amounts: Zinc may be Zinc AAC having a potency between about 15 and 32% and an amount between about 10 and 100 mg; Molybdenum Chelate having a potency between about 12 and 30% and an amount between 0.015 and 0.2 mg; Vitamin B6 (Pyridoxince HCl) having a potency between about 70 and 95% and an amount between about 18 and 170 mg; Amino Acids having a potency of between 90 and 100% and an amount between 25 and 500 mg; cellulose between 100 and 1000 mg; Magnesium Stearate between about 2 and 50 mg; and Dicalcium Phosphate between about 10 and 500 mg.

Example 2

In an office trial, 43 patients with various stages of severe myofascial pain syndrome (fibromyalgia), many with severe vascular headaches, were treated with a daily combination supplement having a formula designed ideally to repair or aid metallothionein functionality, as follows:
  zinc picolinate 50 mg
  natural molybdenum chelate 100 mg
  pyridoxine 25 mg
  boron 3 mg
  serine 25 mg
  glutathione GSH 550 mg
  cystine (NAC) 25 mg
  ornithine 25 mg All 43 patients reported past diagnosis of fibromyalgia (many with chronic severe headaches of various sorts), and all 43 had moderately to severely high NCC copper levels, and all reported significant pain and trigger points. After and during therapy, 41 of 43 reported a significant improvement in pain, headaches, and resolution of trigger points—approaching nearly 95% reduction overall (many with almost complete resolution of pain). The endpoint of the trial was modification of pain levels.

In various embodiments, the amounts may be adjusted depending on the effect on any given individual, as well as the biometrics of that individual. For example, a larger person may require a higher dose than a smaller person. Similarly, a person suffering from acute copper toxicity may benefit from a higher dose for a time until the toxicity is controlled, at which point a lower dose may provide sufficient management over time.

In addition to the disclosed embodiments, other embodiments may be employed in other specific forms without departing from its structures, methods, or other essential characteristics as broadly described and claimed. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A composition for reducing heavy metal accumulation in a user, the composition comprising:
  an amino acid;
  an effective amount of molybdenum chelate for forming a molybdenum cofactor to serve as a catalytic site for molybdenum enzymes in the user;
  pyridoxine;
  an effective amount of zinc for regulating pyridoxine metabolism in the user; and
  reduced glutathione (GSH);
  wherein the composition promotes increased production of metallothionein in the user wherein the amino acid is an effective amount of an amino acid selected from the group consisting of n-acetylcysteine, serine, and glutamine for increasing production of glutathione in the user.

2. The composition of claim 1, wherein the effective amount of zinc is an effective amount of zinc amino acid chelate "AAC" having a potency between about 15% and about 32%.

3. The composition of claim 1, wherein the molybdenum chelate has a potency between about 12% and about 30%.

4. The composition of claim 1, further comprising cellulose, magnesium stearate, and dicalcium phosphate.

5. The composition of claim 1, wherein the reduced glutathione (GSH) is present in an amount effective for reducing a concentration of copper in the user.

6. The composition of claim 1, wherein the effective amount of zinc has a potency between about 15% and about 32% and an amount between about 10 mg and about 100 mg.

7. The composition of claim 1, wherein the effective amount of molybdenum chelate has a potency between about 12% and about 30% and an amount between about 0.015 mg and about 0.2 mg.

8. The composition of claim 1, wherein the pyridoxine has a potency between about 70% and about 95% and an amount between about 18 mg and about 170 mg.

9. The composition of claim 1, wherein the amino acid comprises serine.

10. The composition of claim 1, wherein the amino acid has a potency between about 90% and about 100% and an amount between about 25 mg and about 500 mg.

11. A composition for reducing heavy metal accumulation in a human, the composition comprising:
   an effective amount of zinc picolinate for regulating vitamin B6 metabolism in the human;
   an effective amount of a bio-available form of molybdenum chelate for forming a molybdenum cofactor to serve as a catalytic site for molybdenum enzymes in the human;
   pyridoxine;
   an effective amount of boron for increasing production of ceruloplasmin in the human;
   reduced glutathione (GSH); and
   at least one amino acid;
   wherein the composition promotes increased production of metallothionein in the human wherein the at least one amino acid is an effective amount of an amino acid selected from the group consisting of n-acetylcysteine, serine, and glutamine for increasing production of glutathione in the user.

12. The composition of claim 11, wherein the effective amount of the bio-available form of molybdenum chelate has a potency between about 12% and about 30% and an amount between about 0.015 mg and about 0.2 mg.

13. The composition of claim 11, wherein the pyridoxine has a potency between about 70% and about 95% and an amount between about 18 mg and about 170 mg.

14. The composition of claim 11, wherein the at least one amino acid is serine.

15. The composition of claim 14, wherein the at least one amino acid has a potency between about 90% and about 100% and an amount between about 25 mg and about 500 mg.

16. The composition of claim 11, wherein the effective amount of zinc picolinate has a potency between about 15% and about 32% and an amount between about 10 mg and about 100 mg.

17. The composition of claim 11, wherein the effective amount of boron is in an amount of less than about 3 mg.

18. The composition of claim 1, further comprising an effective amount of boron for increasing production of ceruloplasmin in the user.

\* \* \* \* \*